United States Patent [19]

Franklin

[11] Patent Number: 4,548,728

[45] Date of Patent: Oct. 22, 1985

[54] MASK CLEANSER CONTAINING OATMEAL, POWDERED MILK, BAKING SODA AND HONEY

[76] Inventor: Bernice E. Franklin, 4906 Adelia Dr., Chattanooga, Tenn. 37416

[21] Appl. No.: 710,088

[22] Filed: Mar. 11, 1985

[51] Int. Cl.$^4$ .................. A61K 7/02; C11D 7/40; C11D 7/44; C11D 7/46
[52] U.S. Cl. .................. 252/174.14; 252/89.1; 252/132; 252/173; 252/174.17; 252/DIG. 5; 252/DIG. 14; 514/775; 514/777; 514/783; 514/844; 514/846; 514/847
[58] Field of Search .............. 252/89.1, 132, 173, 252/174.14, 174.17, DIG. 5, DIG. 14; 424/70; 426/551, 556, 618, 619, 620; 514/775, 783, 844, 846, 847, 777

[56] References Cited

U.S. PATENT DOCUMENTS

| | | | |
|---|---|---|---|
| 1,550,026 | 7/1923 | Goode | 424/62 |
| 1,634,974 | 8/1925 | Bucci | 424/357 |
| 1,668,503 | 9/1926 | Hall | 424/364 |
| 1,995,663 | 8/1934 | Bollmann | 424/69 |
| 2,436,818 | 5/1945 | Musher | 424/62 |
| 2,466,261 | 7/1944 | Musher | 106/24 |
| 4,014,995 | 3/1977 | Juliano | 424/168 |
| 4,238,509 | 12/1980 | Evans | 424/358 |
| 4,497,840 | 2/1985 | Gould | 426/560 |

OTHER PUBLICATIONS

Bohn, R. H.; "Biscuit and Cracker Production", 1st. Ed., published by Am. Trade Publishing Co., New York, 1957, pp. 122, 123 & 136–138.

Sagarin, E., et al, Editor, Cosmetics–Science and Technology, 2nd Ed., vol. 1, published by John Wiley & Sons, New York, 1972, pp. 309 & 310.

*Primary Examiner*—Dennis L. Albrecht
*Attorney, Agent, or Firm*—Lamont Johnston

[57] ABSTRACT

A mask cleanser for the hands and other skin surfaces composed of oatmeal, powdered milk, baking soda, honey and water. Two (2) cups of dried oatmeal are blended in a blender with $1\frac{1}{2}$ cups of powdered milk and $\frac{1}{4}$ cup of baking soda until the mixture is powdery fine and smooth. Two thirds ($\frac{2}{3}$) cup of honey and $\frac{1}{2}$ cup of water are added until the mixture forms a paste.

1 Claim, No Drawings

MASK CLEANSER CONTAINING OATMEAL, POWDERED MILK, BAKING SODA AND HONEY

BACKGROUND OF THE INVENTION

This is a mask cleanser for the hands. There is no mask cleanser for the hands commercially available that softens, smooths and cleanses the hands.

DESCRIPTION OF THE PREFERRED EMBODIMENT

The following is the recipe for a mask cleanser made in accordance with my invention:

2 cups dry oatmeal
1½ cups powdered milk
½ cup baking soda (bicarbonate of soda)

Blend these dried ingredients in a blender until the mixture is powdery fine and smooth. Then, add ⅔ cup of honey and 1 cup of water to the mixture to form a paste and pour the paste into a container.

As a mask, apply two or three times a week. Leave on from 15 to 20 minutes. Rinse off with warm water and blot dry.

For dry skin—after using the mask, one can use a moisturizing cream as a base.

As a soap—use on the hands and the entire body, in the shower or bath daily. The results will leave the entire body youthful, silky smooth and refreshed.

This cleanser leaves the skin softer, smoother and more youthful looking. It will also remove dead skin from the hands. One can see the first time it is used. There is no other mask cleanser soap for the hands. You can also use it on your face, legs, your whole entire body, including feet, and see instant results soft to the touch and skin will look more youthful. Most cosmetics for the mask facial say to apply two times a week, leave on 15 to 20 minutes, and rinse off with warm water and blot dry, but my mask cleanser for the hands says rub your hands together and rinse off and dry. Immediately you will see your hands looking smoother, softer and more youthful-looking at once. It is known that oatmeal powder can help soften and smooth the skin; milk can also do the same thing. Baking soda also softens and cleanses the skin leaving the skin with silky feeling. Honey also acts as a cleanser that will cling to the skin drawing off dirt. Mixing all of these together—oatmeal, baking soda, honey and water, works like a miracle on your hands and entire body, which I feel will make this unique because every woman loves beautiful, silky, smooth and youthful looking hands and there is no mask cleanser commercially available for their hands that will help hands to look youthful, softer, silkier, smoother.

Please note that it doesn't take a lot of effort for one to wash his hands. The average person washes the hands from four to five times a day; maybe more. With this product, all one would have to do is use this mask cleanser, instead of a soap, and keep the dead skin from building up on the hands or whatever part of the body one desires. In facial masks, they tell you to use it twice a week to keep the impurities off the skin and to help the skin to look youthful, softer, and cleaner, keeping the pores clean at all times, which we all know will help the face to look youthful, silky and smooth. I repeat—there is nothing commercially available that says to keep the dead skin off your hands and your hands will look youthful, smoother, younger looking, so that is why I say again I believe that we do need a mask cleanser for the hands because every woman loves soft, smooth, silky looking hands.

Other products which are a mask cleanser for the face say to use a cleansing cream first, then rinse off and apply the mask to upward and outward positions on the face and neck. Leave on for 15 to 20 minutes. Many say to lie down and relax with your feet elevated higher than your head. After the 20 minutes is up, you then rinse your face with warm water and you put on an astringent and some say in order to put oil which you have taken out of the skin back into the skin, you should do this the first month 3 times a week. Thereafter, twice a week for the rest of your life if you would like to maintain pretty skin. But, I repeat, there is no mask cleanser for the hands or any other part of the body, including the face and neck, that you squeeze a little bit, rubbing your two hands together and rinse them off and see instant results such as smoother, softer looking hands. Please note that to keep the skin from drying out, you should use a lotion afterwards, which would have to be used even with soap or any cleanser.

This mask cleanser and skin softener soap is so unique because it acts as a cleanser, a mask and a refreshant. It contains dry and natural ingredients that leave the skin youthful, silky smooth and softer. This product will assist in removing impurities from the skin.

There is instant result from the first usage.

I claim:

1. A mask cleanser and skin softener for the hands and other skin surfaces which comprises a mixture of 2 cups of ingredients in the following approximate proportions dry oatmeal, 1½ cups of powdered milk, ½ cup of baking soda with ⅔ cup of honey and 1 cup of water to form a paste.

* * * * *